(12) United States Patent  
Yuzawa et al.

(10) Patent No.: US 8,305,420 B2  
(45) Date of Patent: Nov. 6, 2012

(54) ATTENTION CALLING APPARATUS AND METHOD AND INFORMATION PROCESSING SYSTEM

(75) Inventors: Hideto Yuzawa, Kanagawa (JP); Yoshifumi Matsunaga, Kanagawa (JP); Akinori Komura, Kanagawa (JP); Tomokazu Yago, Kanagawa (JP); Kazuo Shibuta, Kanagawa (JP); Hiroyuki Hattori, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 1759 days.

(21) Appl. No.: 11/219,688

(22) Filed: Sep. 7, 2005

(65) Prior Publication Data

US 2006/0083409 A1    Apr. 20, 2006

(30) Foreign Application Priority Data

Oct. 20, 2004  (JP) .............................. P.2004-305389  
Jun. 17, 2005  (JP) .............................. P.2005-177742

(51) Int. Cl.  
*H04M 11/00*  (2006.01)

(52) U.S. Cl. ..................................... 348/14.01; 455/416

(58) Field of Classification Search .... 348/14.01–14.08, 348/14.09; 370/352; 455/416  
See application file for complete search history.

(56) References Cited

U.S. PATENT DOCUMENTS

| | | | |
|---|---|---|---|
| 6,038,543 A | 3/2000 | Kurosawa | |
| 6,345,111 B1 * | 2/2002 | Yamaguchi et al. | 382/118 |
| 6,606,111 B1 * | 8/2003 | Kondo et al. | 348/14.01 |
| 6,608,644 B1 * | 8/2003 | Kondo et al. | 348/14.09 |
| 7,342,601 B2 * | 3/2008 | Kondo et al. | 348/14.08 |
| 2004/0003042 A1 | 1/2004 | Horvitz et al. | |

FOREIGN PATENT DOCUMENTS

| | | |
|---|---|---|
| JP | 6-95835 A | 4/1994 |
| JP | 7-56748 A | 3/1995 |
| JP | 8-329013 A | 12/1996 |
| JP | 2001-252265 A | 9/2001 |
| JP | 2001-307298 A | 11/2001 |
| JP | 2003-240560 A | 8/2003 |
| JP | 2004-109995 A | 4/2004 |

OTHER PUBLICATIONS

Notification of Reasons for Refusal issued May 11, 2010, in counterpart Japanese Application No. 2005-177742.  
Notification of Reasons for Refusal issued Aug. 10, 2010, in counterpart Japanese Application No. 2005-177742.

* cited by examiner

*Primary Examiner* — Curtis Kuntz  
*Assistant Examiner* — Maria El-Zoobi  
(74) *Attorney, Agent, or Firm* — Sughrue Mion, PLLC

(57) ABSTRACT

An attention calling apparatus includes: a measurement unit for measuring at least one first job related physical quantity related to a performance status of a first job of a user; and an attention calling processing execution unit for executing processing for calling user's attention so as to perform a second job based on the first job related physical quantity measured by the measurement unit and at least one second job related physical quantity indicating a status of the second job which a user can perform.

29 Claims, 17 Drawing Sheets

FIG. 2

| USER | TIME t | PUPIL DIAMETER x | PUPIL DIAMETER y | GAZE TIME | BLINK | ELECTRO-ENCEPHALO-GRAM | FACIAL SKIN TEMPERATURE | ... | ... | ... | ... |
|---|---|---|---|---|---|---|---|---|---|---|---|
| CONFERENCE PARTICIPANT A | 0 | 4 | 4 | 0 | N | 10 | 34 | ... | ... | | |
| CONFERENCE PARTICIPANT | 60 | 5 | 4 | 0 | N | 12 | 34 | | | | |
| | 120 | 8 | 7 | 133 | N | 11 | 36 | | | | |
| | 180 | 8 | 7 | 0 | N | 18 | 36 | | | | |
| | 240 | 8 | 7 | 33 | N | 19 | 36 | | | | |
| | : | : | : | : | : | : | : | | | | |

FIG. 3

| USER | TIME t | UTTERANCE | SOUND VOLUME | ENVIRONMENTAL SOUND VOLUME | ... |
|---|---|---|---|---|---|
| CONFERENCE PARTICIPANT A | 0 | N | 0 | 42 | ... |
| CONFERENCE PARTICIPANT | 60 | N | 0 | 46 | |
| | 120 | Y | 70 | 50 | |
| | 180 | Y | 70 | 40 | |
| | 240 | Y | 0 | 41 | |
| | : | : | : | : | |

FIG. 4

| USER | TIME t | AMOUNT OF KEYBOARD INPUT | AMOUNT OF MOUSE MOVEMENT | ... | | | | | | | | | | |
|---|---|---|---|---|---|---|---|---|---|---|---|---|---|---|
| CONFERENCE PARTICIPANT A | 0 | 10 | 120 | ... | | | | | | | | | | |
| CONFERENCE PARTICIPANT | 60 | 12 | 23 | | | | | | | | | | | |
| | 120 | 70 | 100 | | | | | | | | | | | |
| | 180 | 70 | 20 | | | | | | | | | | | |
| | 240 | 20 | 20 | | | | | | | | | | | |
| | ⋮ | ⋮ | ⋮ | ⋮ | | | | | | | | | | |

FIG. 5

| USER | TIME t | PUPIL DIAMETER x | PUPIL DIAMETER y | GAZE TIME | BLINK | ELECTRO-ENCEPHALO-GRAM | FACIAL SKIN TEMPERATURE | UTTERANCE | SOUND VOLUME | AMOUNT OF KEYBOARD INPUT | AMOUNT OF MOUSE MOVEMENT |
|---|---|---|---|---|---|---|---|---|---|---|---|
| CONFERENCE PARTICIPANT A | 0 | 4 | 4 | 0 | N | 10 | 34 | N | 0 | 10 | 120 |
| CONFERENCE PARTICIPANT | 60 | 5 | 4 | 0 | N | 12 | 34 | N | 0 | 12 | 23 |
| | 120 | 8 | 7 | 133 | N | 11 | 36 | Y | 70 | 70 | 100 |
| | 180 | 8 | 7 | 0 | N | 18 | 36 | Y | 70 | 70 | 20 |
| | 240 | 8 | 7 | 33 | N | 19 | 36 | Y | 0 | 20 | 20 |
| | ⋮ | ⋮ | ⋮ | ⋮ | ⋮ | ⋮ | ⋮ | ⋮ | ⋮ | ⋮ | ⋮ |

FIG. 6

DEGREE OF CONCENTRATION f = w11*PUPIL DIAMETER (AMOUNT OF CHANGE, CHANGE SPEED) + w12*GAZE (TIME, FREQUENCY) + w13*BLINK (RATIO, FREQUENCY, NUMBER OF CLUSTER BLINKS) + w14*AMOUNT OF CHANGE IN FACIAL SKIN TEMPERATURE) + w15*ELECTROENCEPHALOGRAM + w16*UTTERANCE SOUND VOLUME + w17*AMOUNT OF KEYBOARD INPUT + ...

FIG. 8

| USER | TIME t | 0 | 60(t1) | 120 | 180(t2) | 240 | 300 | 360(t3) | 420 | 480 | 540(t4) | 600 | ... |
|---|---|---|---|---|---|---|---|---|---|---|---|---|---|
| | DEGREE OF CONCENTRATION ft | 0.8 | 0.8 | 0.8 | 0.8 | 0.8 | 0.8 | 0.8 | 0.8 | 0.8 | 0.2 | 0.2 | ... |

| CONFERENCE PARTICIPANT A | TIME t | 0 | 60(t1) | 120 | 180(t2) | 240 | 300 | 360(t3) | 420 | 480 | 540(t4) | 600 | ... |
|---|---|---|---|---|---|---|---|---|---|---|---|---|---|
| CONFERENCE PARTICIPANT | DEGREE OF CONCENTRATION fm | 0.2 | 0.2 | 0.2 | 1.0 | 1.0 | 0.2 | 0.4 | 0.4 | 0.4 | 0.4 | 0.4 | ... |

| TIME t | t1 | t2 | t3 | t4 |
|---|---|---|---|---|
| DEGREE OF CONCENTRATION ft | 0.8 | 0.8 | 0.8 | 0.2 |
| DEGREE OF CONCENTRATION fm | 0.2 | 1.0 | 0.4 | 0.4 |
| fm(t)−ft(t) | −0.6 | +0.2 | −0.4 | +0.2 |
| ft(t)−ft(t−1) | 0 | 0 | 0 | −0.6 |
| SWITCHING TIMING | × | ◎ | △ | □ |

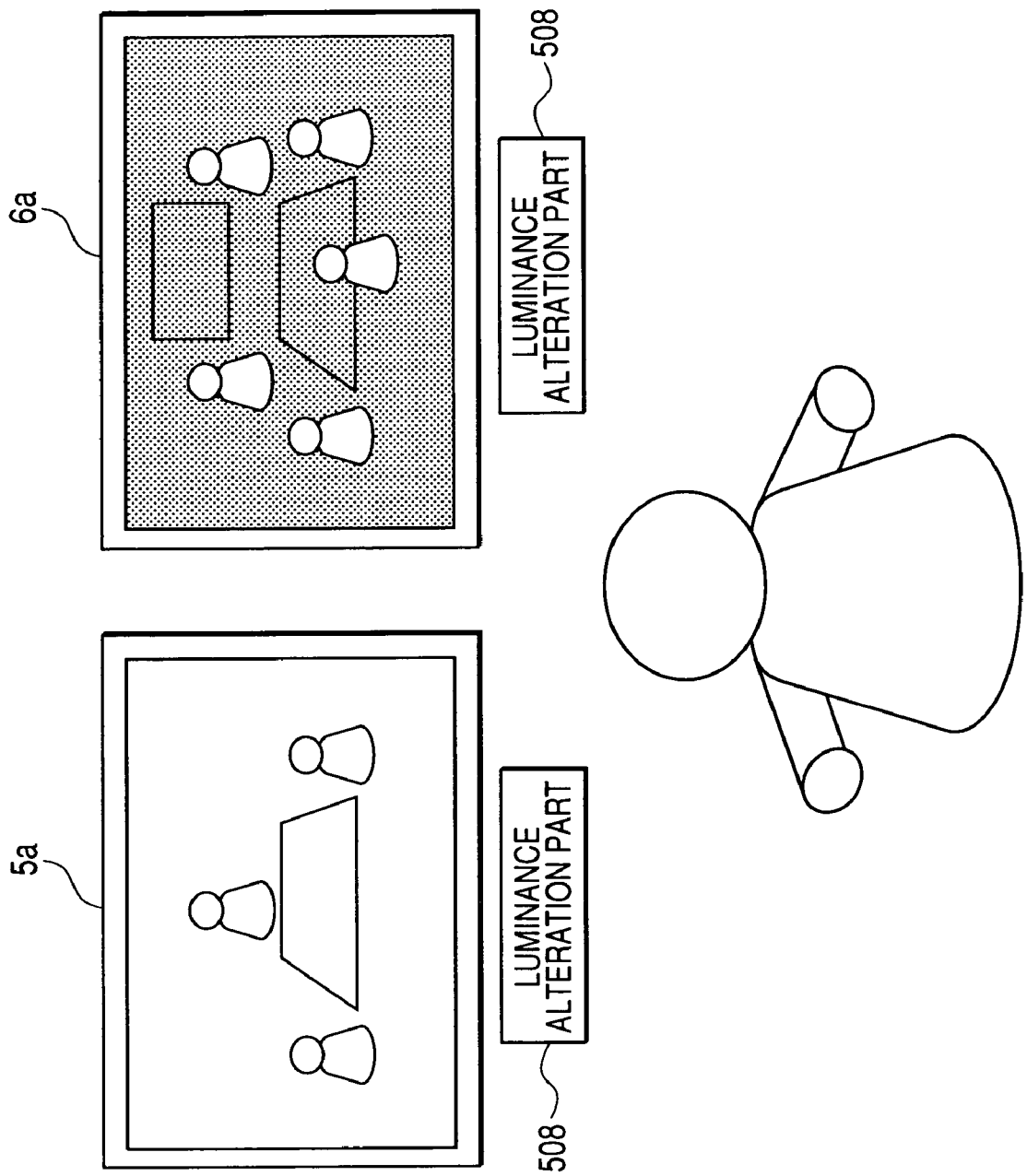

ATTENTION CALLING APPARATUS AND METHOD AND INFORMATION PROCESSING SYSTEM

BACKGROUND OF THE INVENTION

1. Field of the Invention

The present invention relates to an attention calling technique for calling attention so as to switch job performance from a predetermined job to another job, and particularly to a technology constructed so that an actual status of jobs can be reflected to do switching of the optimum job performance.

2. Background Art

Conventionally, in a job (also called a task) in an office, it has been required that plural jobs including a communication job should be executed in parallel. Particularly when in recent years, information is linked by networks and the information can further be accessed from anywhere by mobile environment, a scene in which while a user performs one job, communication is requested from other persons and a new job is requested increases. Therefore, it becomes important to perform plural jobs efficiently without causing trouble mutually.

Incidentally, techniques related to the invention are as follows.

JP-A-07-56748 proposes that active/inactive statuses, information about starting of plural applications are monitored and execution orders of plural tasks are controlled. For example, when desired mail comes in the case that a certain job is in a mail wait status, a user is notified that the job can be processed.

JP-A-06-95835 proposes automatic navigation in which a window including a retrieval criterion specified by a user is activated in multi-window environment.

However, in the apparatus described in JP-A-07-56748, it is targeted for the active/inactive statuses of the applications and it is difficult to deal with communication jobs (TIMESPACE IN THE WORKPLACE: DEALING WITH INTERRUTIONS, Brid O'Conaill and David Frohlich, Hewlett Packard Labs.) which occupy many of the office jobs and probably tend to interrupt an individual job. Even in the case of grasping that a community site of a mail base is communication environment, it is unnecessary to direct attention to all the moments at which writings were performed, and presentation of this to a user may result in interruption of an individual job in reverse.

Also, in the apparatus described in JP-A-06-95835, it is targeted for an application and it is difficult to deal with communication jobs and further it can be applied to a job using a WEB site in which an interest item can be preset, but it is very difficult to apply this to a form of a conference in which the contents vary dynamically and further in the case of supporting simultaneous progress of plural jobs, it is essentially necessary to consider a balance with a status of performance of an individual job and the conventional technique is lacking in this support.

SUMMARY OF THE INVENTION

The invention has been implemented in consideration of the circumstances as described above, and an object of the invention is to provide an attention calling technique constructed so that an actual status of jobs can be reflected to do switching of the optimum job performance. More specifically, an object of the invention is to provide a technique for displaying proper task switching timing and notifying a user of the timing from a status of communication conducted in the periphery including a remote site and a status of job performance of the user in a scene in which plural routine jobs including a communication job are performed in parallel.

Also, in further advance of the above, an object of one aspect of the invention is to provide the attention calling constructed so that an actual status of jobs can be reflected to do switching of the optimum job performance so as not to interfere with the primary job.

According to the principle configuration example of the invention, in order to achieve the objects described above, a control apparatus is provided with a synchronization unit for synchronizing a job performance status of a user including biological information and a job status including biological information of a person involved in a peripheral job, and a determination unit for determining a possibility of plural work execution of a user based on information synchronized by the synchronization unit. Predetermined display is carried out by a display unit according to a determination result.

In this configuration, for example, based on biological information, audio information, task log information about a user of the deskwork side and biological information, communication information about a person present in communication environment, switching of a job (task) can be done and also it is determined whether or not the switching is required, so that plural jobs can be performed simultaneously efficiently.

The synchronization unit is a portion capable of momentarily comparing an index (for example, the degree of concentration) of a job performance status of a user with an index (for example, the degree of concentration) of a job status of a person involved in a peripheral job on the same time axis.

The control apparatus is typically a personal computer for job performance, but is not limited to this.

In this configuration, the determination unit, for example, estimates psychological states of the person involved in the peripheral job and the user and determines plural job statuses based on information about the synchronization unit.

Also, the synchronization unit is configured to include, for example, a deskwork status detection unit for detecting biological information, audio information, job status information, etc. as a job performance status of a user, and a peripheral job status detection unit for detecting biological information, audio information, job status information, etc. about a person performing a job in the periphery, and synchronize information acquired by the deskwork status detection unit and information acquired by the peripheral According to one aspect of the invention, in order to achieve the objects described above, it is constructed so that an attention calling apparatus is provided with a measurement unit for measuring at least one first job related physical quantity related to a performance status of a first job of a user, and an attention calling processing execution unit for executing processing for calling user's attention so as to perform a second job based on the first job related physical quantity measured by the measurement unit and at least one second job related physical quantity indicating a status of the second job which a user can perform.

In this configuration, a user can be prompted to do switching of jobs properly based on the physical quantities indicating statuses of plural jobs.

The physical quantity is the quantity capable of being measured according to the natural laws, and includes distribution, frequency, etc. of an event without being limited to temperature, time, sound volume, etc.

In this configuration, it may be constructed so that the attention calling processing execution unit also executes processing for calling user's attention so as to perform the first job. That is, in the case of deciding that switching from the second job to the first job is proper, it is prompted to do this. Of course, it may be prompted to do switching from the second job to the first job by another attention calling processing execution unit. Also, it may be constructed so as not to be prompted to do switching from the second job to the first job.

Also, the second job related physical quantity can be set at a physical quantity indicating a performance status of the second job of a person constructing a status of the second job.

In this case, a physical quantity indicating a performance status of the second job obtained for a person selected from among plural persons constructing a status of the second job may be used. For example, a lecturer in a lecture, the chair, atypical viewer representative, etc. can be selected. Polling etc. may be carried out in a state capable of acquiring information from plural persons.

Also, a physical quantity indicating a performance status of the second job obtained for plural persons constructing a status of the second job may be used. Thus, variations can be avoided.

Also, the first job related physical quantity and the second job related physical quantity are typically a physical quantity indicating the degree of human concentration on a job.

The physical quantity indicating the degree of human concentration on the job is typically selected from the group including human biological information, human audio information and human operation processing information, but is not limited to this.

The human biological information is typically selected from the group including an electroencephalogram, utterance information, facial skin temperature and information about an eyeball including a blink, a pupil diameter, a gaze target and gaze time, but is not limited to this.

The human biological information can preferably be measured without attaching a measuring device to a human of a target.

The human audio information is typically detected by an audio detector such as a microphone, but is not limited to this.

The human operation processing information is typically selected from the group including video information, key input information and mouse operation input information, but is not limited to this.

Generally, a measurement unit for measuring the second job related physical quantity is further disposed. However, when the second job is a job etc. of viewing video contents, information about the video contents can also be used as a measurement result as it is.

The first job is typically deskwork using a personal computer etc., but is not limited to this.

The second job is typically a job involving communication, but is not limited to this.

The job involving the communication is, for example, a job of a conference using a teleconference system or a conference attending a conference place.

The second job is, for example, a job requiring a human audio-visual action or viewing of audio-visual contents.

The attention calling processing is typically selected from the group including display on a display device, pronunciation by a pronunciation device and generation of smell by a smell generation device, but is not limited to this.

Also, it may be constructed so that the first job and the second job are executed in a window of a multitasking and multi-window system, and a window of the first job is activated based on a response input of a user to the attention calling processing or by the attention calling processing.

Also, the attention calling processing is preferably processing for suppressing interference with at least the first job.

In other words, the attention calling processing is preferably processing for calling attention through a sensory organ other than a sensory organ mainly used in at least the first job.

By being constructed thus, the attention calling constructed so that an actual status of jobs can be reflected to do switching of the optimum job performance can be executed so as not to interfere with the primary job. More specifically, in a scene in which plural routine jobs including a communication job are performed in parallel, proper task switching timing can be executed so as not to interfere with an audio-visual function of a person used in the primary job.

The attention calling processing can be set at, for example, at least one of vibration by a vibration generation device, change in temperature by a heat transfer device, change in air volume by a blower, and change in a display position by a display position alteration device.

Also, the attention calling processing may be processing for suppressing a physical quantity presented in relation to one job which does not require attention calling. For example, the processing for suppressing a physical quantity presented in relation to one job is at least one of alteration in sound volume, alteration in sound quality, alteration in luminance, and alteration in image quality. Also in this case, the attention calling constructed so that an actual status of jobs can be reflected to do switching of the optimum job performance can be executed so as not to interfere with the primary job.

Also, the attention calling processing may be processing for delaying information related to one job which does not require attention calling by inserting blank time. Presentation of information suspended with the delay may be resumed ex post facto, or may be discarded and resumed in the middle.

The attention calling apparatus of the invention may be constructed as an apparatus received in a single cabinet or may be constructed by combining plural devices distributed and arranged. For example, the attention calling apparatus may be mainly constructed of a client device and a server device connected by a communication network.

Incidentally, the invention can be implemented as a method as well as an apparatus or a system. Also, it goes without saying that apart of the invention can be constructed as software. Also, a software product used for making a computer execute such software is naturally included in the technical scope of the invention.

According to the invention, an actual status of jobs can be reflected to do switching of the optimum job performance. More specifically, a user can simultaneously perform plural jobs by presenting proper switching timing in routine jobs including a communication job.

BRIEF DESCRIPTION OF THE DRAWINGS

These and other objects and advantages of this invention will become more fully apparent from the following detailed description taken with the accompanying drawings in which:

FIG. 2 is a diagram describing an example of biological information on the first embodiment;

FIG. 3 is a diagram describing an example of audio information on the first embodiment;

FIG. 4 is a diagram describing an example of job status information on the first embodiment;

FIG. 5 is a diagram describing a combination example of each information on the first embodiment;

FIG. 6 is a diagram describing an example of a concentration degree identification function used in the first embodiment;

FIG. 8 is a diagram describing an example of concentration degree time response of the first embodiment;

FIG. 18 is a diagram further describing an example of another technique for calling attention by altering an audio-visual form in the second embodiment.

DETAILED DESCRIPTION OF THE PREFERRED EMBODIMENTS

Embodiments of the invention will be described below.

First Embodiment

First, a first embodiment of the invention will be described. The first embodiment relates to a display system 100 for simultaneously carrying out deskwork processing and peripheral job processing.

Figure 1:
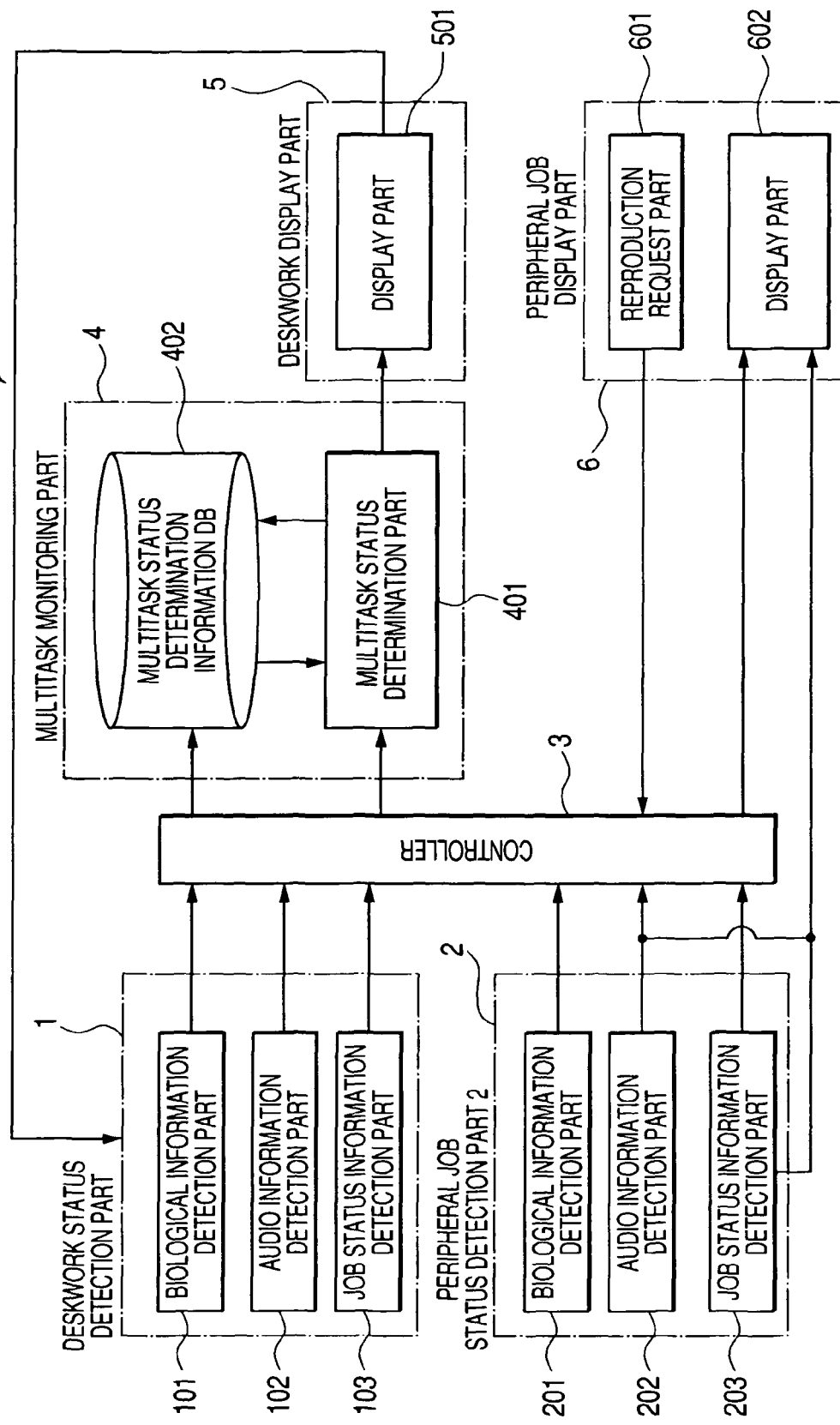
FIG. 1 is a diagram showing a first embodiment of the invention by functional blocks.

FIG. 1 is a diagram schematically showing a configuration of functions of detection, preservation and display in the display system 100 according to the present embodiment. As shown in FIG. 1, the display system (attention calling apparatus) 100 includes a deskwork status detection part (a measurement unit) 1, a peripheral job status detection part 2, a controller 3, a multitasking monitoring part 4, a deskwork display part (an attention calling processing execution unit) 5 and a peripheral job display part 6.

The deskwork status detection part 1 is constructed of a biological information detection part 101, an audio information detection part 102 and a job status information detection part 103. The peripheral job status detection part 2 is constructed of a biological information detection part 201, an audio information detection part 202 and a job status information detection part 203. The multitasking monitoring part 4 is constructed of a multitasking status determination part 401 and a multitasking status determination information database 402. The deskwork display part 5 is constructed of a display part 501. The peripheral job display part 6 is constructed of a reproduction request part 601 and a display part 602.

The display system 100 is a system for displaying switching timing of plural jobs.

This display system 100 is broadly divided into a portion for synchronizing information in which a status of deskwork is recorded and preserved together with detection of biological information, audio information and job status information and a portion in which a status of a peripheral job is recorded and preserved together with detection of biological information, audio information and job status information, a portion for determining a status of performance of plural jobs from the synchronized information, and a portion for carrying out display based on that determination.

The deskwork status detection part 1 is a portion for detecting a status of deskwork, and includes the biological information detection part 101, the audio information detection part 102 and the job status information detection part 103 as described above. The biological information detection part 101 detects biological information such as an electroencephalogram, utterance information, facial skin temperature, or information about an eyeball, for example, a blink, a pupil diameter, a gaze target, gaze time of a user during deskwork. It is preferable that the biological information acquired herein can particularly be acquired without attachment of a measuring device to the user.

For example, information about the pupil diameter or the blink can be acquired by a unit for measuring the pupil diameter or a unit for extracting a face region from a face image in which a face of a viewer is imaged by a camera using a publicly known technique (JP-A-2001-100888) and further specifying an eye region and counting the number of blinks. The gaze target and the gaze time can be acquired by using an image imaged with a camera etc. arranged in the side of a gaze target candidate and specifying an eye region by the technique and specifying the gaze target from a position of the camera imaged and specifying the gaze time from imaging time of the eye region imaged. The facial skin temperature can be acquired by an infrared camera, thermography, etc. without attachment of a measuring device to a viewer.

The audio information detection part 102 is a portion for detecting audio etc. of a user in order to recognize a job status of a user of the deskwork side. This audio information detection part 102 can be used by properly selecting a general audio detector such as a sound collection microphone.

The job status information detection part 103 is a portion for detecting a deskwork status of a user. The job status information detection part 103 can be used by properly selecting a general video information detector such as a video camera. A camera capable of imaging a situation on a desk, documents displayed on a display or a user, etc. at a wide angle is preferably used in this job status information detection part 103. Or, for a job using a computing machine, an operation log acquisition unit on a general computing machine, for example, an application starting status, a keyboard input status or a mouse operation status can be used.

The peripheral job status detection part 2 is a portion for detecting a status of the peripheral side, and includes the biological information detection part 201 for a peripheral job performer including a communication job, the audio information detection part 202 and the job status information detection part 203 as described above. The biological information detection part 201 has a function similar to that of the biological information detection part 101. The audio information detection part 202 has a function similar to that of the audio information detection part 102. The job status information detection part 203 is a portion for detecting a peripheral job status. The job status information detection part 203 can be used by properly selecting a general video information detector such as a video camera. A camera capable of imaging presentation documents used in a conference or a viewer, etc. at a wide angle is preferably used in this job status information detection part 203.

In the biological information, data acquired by the biological information detection parts 101, 201 is held as, for example, a data sheet of a table format.

FIG. 2 is a diagram showing an example in which biological information is held in a data sheet of a table format. In this data sheet, biological information such as time t, pupil diameters x, y, a gaze target, gaze time, a blink, facial skin temperature and an electroencephalogram is held every, for example, user or conference participant. Particularly, in the gaze target, the gaze target is formed by specifying a camera position capable of being imaged from a camera installed in the gaze target side. The gaze time is recorded by calculating accumulation time every each target. A representation method is not limited to this, and may be a graph format etc.

FIG. 3 is a diagram showing an example in which audio information is held in a data sheet of a table format. In the audio information, data acquired by the audio information detection part 102 and the audio information detection part 201 is held as, for example, a data sheet of a table format. The audio information such as time t, the presence or absence of utterance, sound volume and environmental sound is held every, for example, viewer. A representation method is not limited to this, and may be a graph format etc.

FIG. 4 is a diagram showing an example in which job status information is held in a data sheet of a table format. In the job status information, data acquired by the job status information detection parts 103, 203 is held as, for example, a data sheet of a list format. A representation method is not limited to this.

The controller 3 synchronizes biological information data, audio information data and job status information data detected by the deskwork status detection part 1 and the peripheral job status detection part 2, and holds this synchronized information. A recording function of this controller 3 can be used by properly selecting a general recorder such as a semiconductor memory, a hard disk or a flexible disk. The data synchronized by the controller 3 herein is held as, for example, a data sheet of a table format.

FIG. 5 is a diagram showing its data sheet. In this data sheet, the biological information such as time, pupil diameters, a gaze target, gaze time, a blink and facial skin temperature, the audio information such as time, the presence or absence of utterance, sound volume, the presence or absence of utterance of a speaker, sound volume of a speaker and environmental sound, and the job status information data are held every, for example, viewer. A representation method is not limited to this.

The multitasking monitoring part 4 is constructed by properly selecting a general recorder such as a semiconductor memory, a hard disk or a flexible disk capable of holding an indexed file and a CPU capable of carrying out state estimation processing.

The multitasking status determination part 401 carries out processing for estimating psychological states of a conference participant and a user in deskwork using a predetermined psychological state identification function based on the file. The psychological states of this user and a conference viewer include, for example, mental information or a cognitive state of the conference viewer. Specifically, the multitasking status determination part 401 calculates the degree of concentration of the user and the viewer using the identification function. This identification function weights and adds biological information, audio information and job status information about the user and the conference participant. In this multitasking status determination part 401, its function is implemented by executing a predetermined program. This multitasking status determination part 401 uses a parameter. Data described in a file held and integrated by the controller 3 is used in this parameter. This parameter includes, for example, a state of the degree of concentration of the user and the viewer.

Eyeball movement psychology (experimental psychology of eyeball movement, psychology of blinks, psychology of pupil movement) probably shows that interest is related to pupil diameters and levels of understanding and memory are related to blinks and levels of excitement and comfort are related to blinks or facial skin temperature. However, in each of these, accuracy cannot be maintained, for example, an increase in facial skin temperature because of indoor temperature environment. Therefore, the state is identified by an evaluation function of weighting and adding these data and utterance sound volume, environmental sound, etc.

FIG. 6 is a diagram describing the identification function. In FIG. 6, w shows a weighting factor. For example, when the amount of change in a pupil is large and gaze time is long and the number of blinks is small and the amount of change in facial skin temperature is large and utterance sound volume is large in the degree f of concentration, there is a high possibility that attention has been directed. Or, beta waves probably show a thinking state in an electroencephalogram, and have a high possibility that attention has been directed. Using this, a psychological state is specified. As a result of this, the degree f of concentration is identified by weighting and adding pupil diameters (the amount of change, change speed), a gaze (time, frequency), a blink (ratio, frequency, the number of cluster blinks), the amount of change in facial skin temperature, utterance sound volume, utterance sound volume of a speaker, environmental sound, the amount of key input, etc, by means of weighting factors w11 to w1n, respectively.

A situation in which shift necessary candidates of consciousness become enormous and the capability remarkably degrades can be prevented always by presenting proper switching timing for simultaneous progress of plural jobs by threshold setting.

At timing of satisfying a predetermined determination condition using an estimation result by the multitasking monitoring part 4, the display part 501 displays the fact in a predetermined format. As a display form, for example, a graphical display format by icons is used. In addition to the graphical display format by icons, a sound signal presentation format by a call sound or a mechanical signal sound may be adopted. Further, it may be constructed so that it focuses on the sense of smell in which it is not expected that a human sensory organ required in the primary job (for example, participation in a conference or deskwork) will be used in many cases and smell is set for attention calling and a smell component is generated from the corresponding job information side and attention is called.

The reproduction request part 601 can be constructed of, for example, a touch panel, a mouse or a keyboard. As a result of this, for example, when a conference is conducted as communication environment, intention or a flow of talk can be checked tracing time to the point slightly before the switching timing in the case of wanting to check the intention or the flow.

By this display, a desired scene can be reviewed efficiently.

Incidentally, it can be decided whether a user is performing a job of deskwork or is performing a peripheral job from a state etc. of an application process or a gaze target of the user.

Next, an action of the display system 100 will be described.

Figure 7:
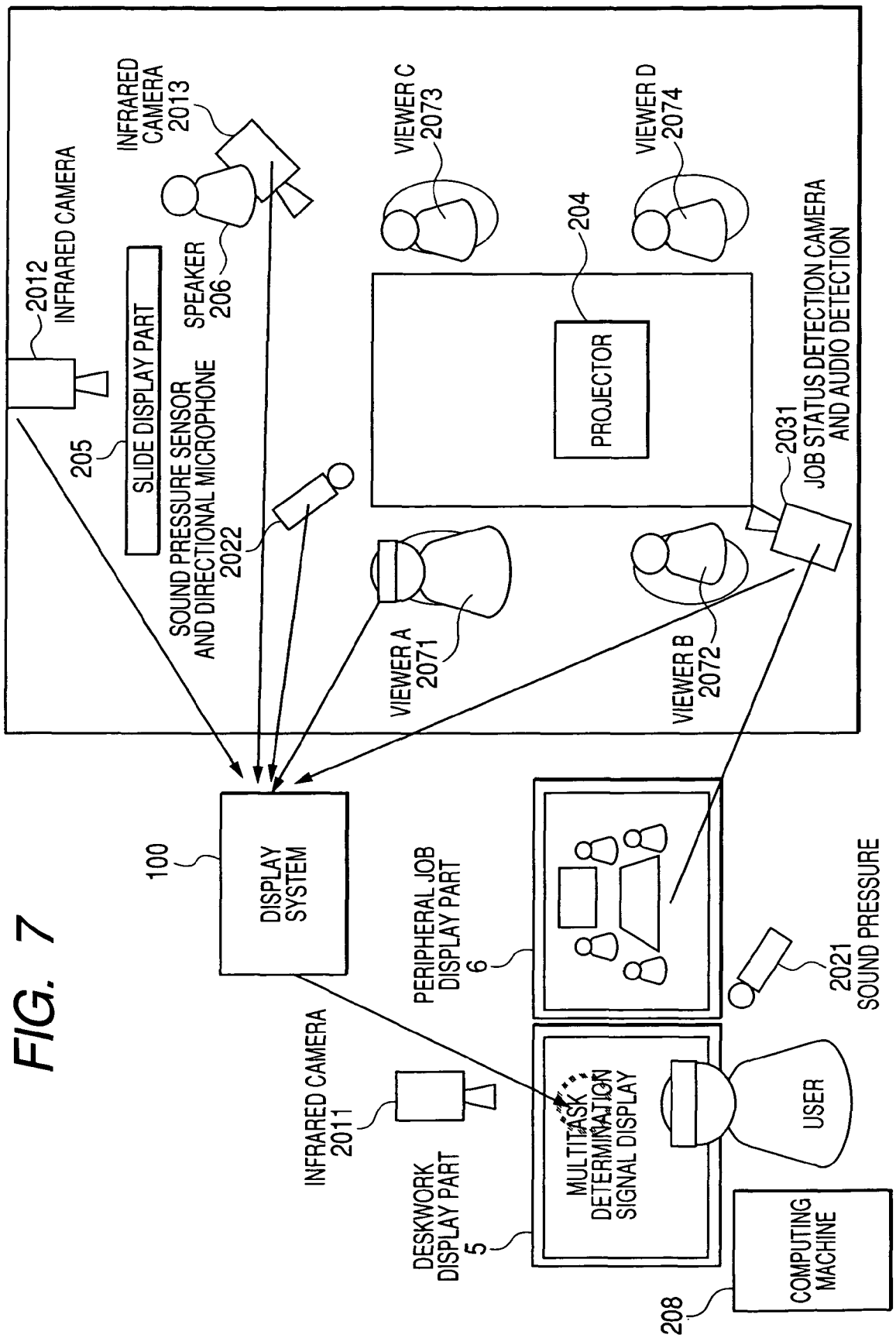
FIG. 7 is a diagram describing a specific configuration example of the first embodiment.

Here, display and detection of biological information, audio information and job status information will be first described according to a configuration example as shown in FIG. 7. In the display system 100 of FIG. 7, a biological information detection part 101 (infrared camera 2011) detects biological information such as facial skin temperature or information about an eyeball, for example, a blink, a pupil diameter, a gaze target, gaze time in deskwork of a user. Specifically, the biological information detection part 101 is constructed of the infrared camera 2011. As a result of this, for example, when a user gazes at a deskwork display part 5, eyeball video is detected by the infrared camera 2011.

An audio information detection part 102 is constructed of, for example, a sound pressure sensor and a directional microphone 2021. As a result of this, for example, utterance information about a user is detected.

A job status information detection part 103 is constructed of a computing machine 208. As a result of this, a deskwork log (key input or mouse operation, etc.) of a user is detected. Data acquired by the biological information detection part 101 is held as the data sheet of the table format shown in FIG. 2. Data acquired by the audio information detection part 102 is held as the data sheet of the table format shown in FIG. 3. Data acquired by the job status information detection part 103 is held as the data sheet of the table format in FIG. 4.

In this example, presentation is carried out by a speaker 206 using a projector 204 and a slide display part 205. On the ground, viewers (A to D) 2071 to 2074 are viewing this presentation. The contents of the presentation are photographed by a job status detection camera and audio detection 2031. A user can view the contents of the presentation by a peripheral job display part 6.

Also in a biological information detection part 201 of a peripheral job status detection part 2, detection is carried out in a manner similar to that of the biological information detection part 101.

An audio information detection part 202 is constructed of, for example, a sound pressure sensor and a directional microphone 2022.

A job status information detection part 203 is constructed of, for example, a camera 2031 to which an audio detection function is added.

A controller 3 synchronizes biological information, audio information and job status information detected by the biological information detection part 101, the audio information detection part 102, the job status information detection part 103, the biological information detection part 201, the audio information detection part 202 and the job status information detection part 203, and records the information as a file.

Incidentally, a display method according to the invention is implemented using, for example, a CPU (Central Processing Unit), ROM (Read Only Memory), RAM (Random Access Memory), etc., and a program is installed from a hard disk device or a portable storage medium such as a CD-ROM, a DVD or a flexible disk, or is downloaded from a communication circuit and the CPU executes this program and thereby each of the steps is implemented.

The degree $fm(t)$ of concentration on a peripheral job status and the degree $ft(t)$ of concentration on a deskwork status specified by the concentration degree identification function (FIG. 6) are shown by a table format in FIG. 8.

Figure 9:
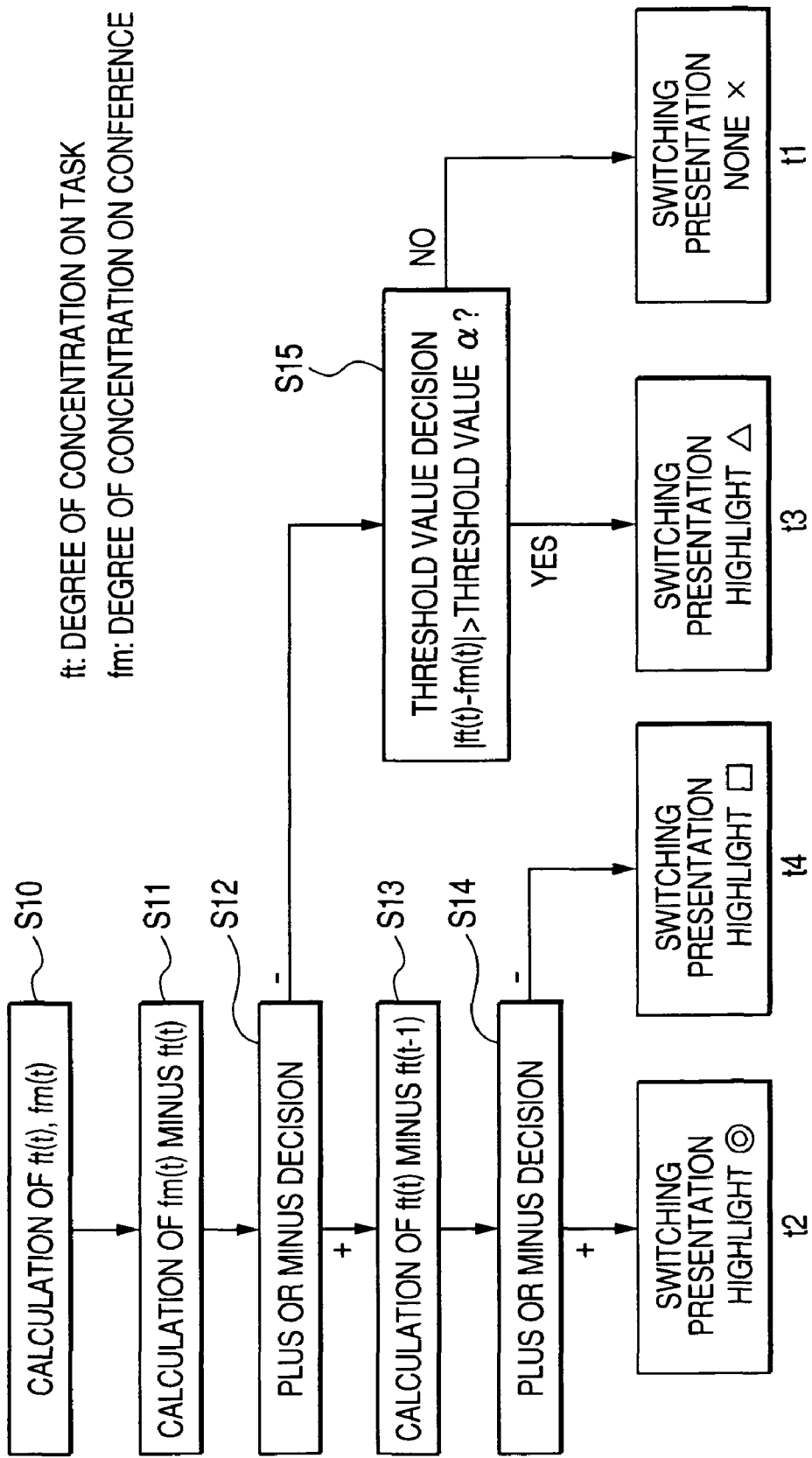
FIG. 9 is a flowchart describing an example of an action of the first embodiment.

A flow of multitasking status determination is shown in FIG. 9. First, ft and fm are respectively specified by the concentration degree identification function (S10). The fm may depend on, for example, a key person of conference participants or may use an average of plural persons. Next, by calculation of $fm(t)$ minus $ft(t)$, the superiority status is specified (S11, S12). It is considered that the need for switching display is large when the degree $fm(t)$ of concentration on a peripheral job status is superior herein. Further, a tendency to decrease the degree of concentration on deskwork is determined by calculation of $ft(t)$ minus $ft(t-1)$ (S13). That is, it is specified whether the degree of concentration on the peripheral job has increased without depending strongly on the degree ft of concentration or it is determined that the degree fm of concentration on the peripheral job is relatively high because the degree ft of concentration on the deskwork has decreased (tired). In view of this result, a display method can be altered. Also, even when ft is superior in a plus or minus decision on $fm(t)$ minus $ft(t)$, the need for switching is displayed by referring to a threshold value (S15). At this time, the need for switching is eliminated in the case of falling below the threshold value.

Figures 10, 11:
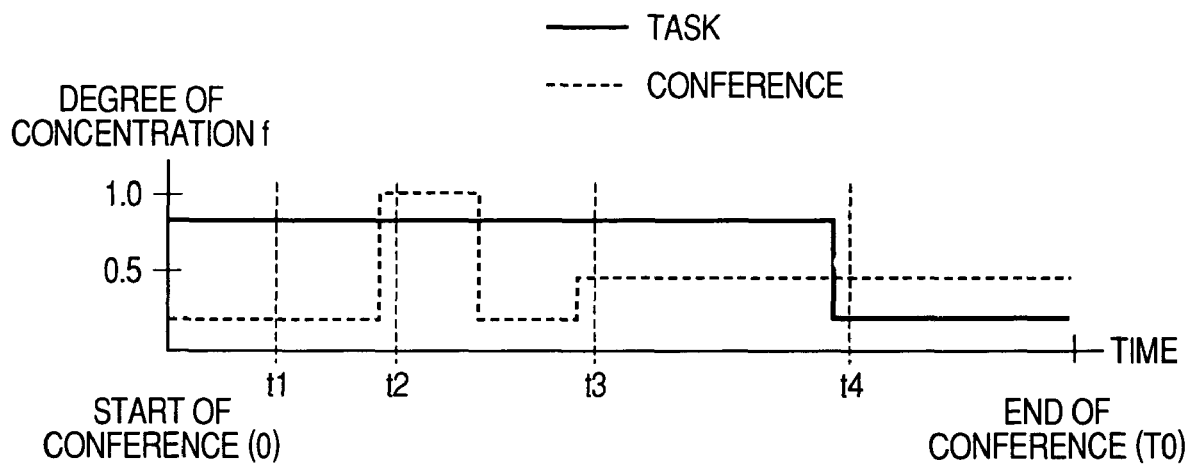
FIG. 10 is a diagram describing the switching timing of the first embodiment.
FIG. 11 is a diagram describing an example of switching presentation decision results of the first embodiment.

FIG. 10 is a diagram schematically representing switching timing of the present system. At t1 in the drawing, in the flow of multitasking status determination, the need for switching presentation is rejected and display is not required. At t2, fm becomes superior and a switching highlight is set high and is displayed. At t3, ft is superior but in the case of being a threshold value or more, in consideration of that fact, a highlight is decreased and the need for switching is displayed. It is determined that the degree of concentration on a deskwork job has decreased and fm has become superior relatively at t4, and in consideration of that fact, the need for switching is displayed. As a result of this, change of pace can be made simply. By a series of these processing, the switching timing is displayed by a proper highlight at the timing of t2, t3 and t4. A list of results is shown in FIG. 11.

Second Embodiment

Next, a second embodiment of the invention will be described with reference to FIG. 12. Incidentally, in FIG. 12, the description is omitted by attaching corresponding numerals to places corresponding to those of FIG. 1.

In the second embodiment, an interference avoidance type display part 502 is disposed instead of the display part 501 of the first embodiment. As described above, the display part 501 of the first embodiment is a portion for displaying the fact in a predetermined format at timing of satisfying a predetermined determination condition using an estimation result by the multitasking monitoring part 4 and, for example, a graphical display format by icons or a sound signal presentation format by a call sound or a mechanical signal sound are adopted. Depending on aspects of such attention calling presentation formats, a human sensory organ required in the primary job (for example, participation in a conference or deskwork) is used, so that there is fear of interfering with the primary job and applying a further recognition load to a user. The interference avoidance type display part 502 of the second embodiment adopts a presentation unit for avoiding such interference with the primary job.

Figure 12:
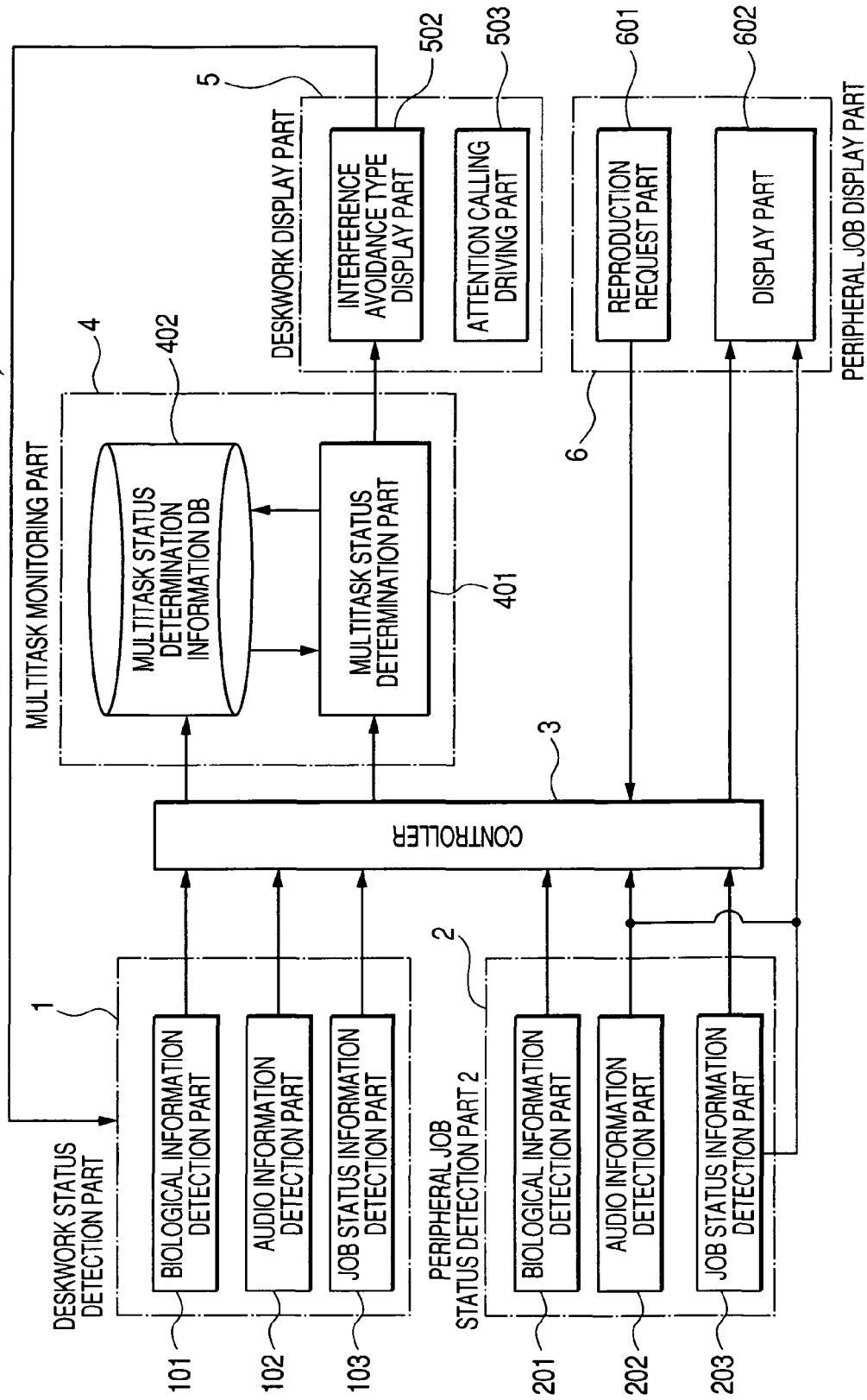
FIG. 12 is a diagram showing a second embodiment of the invention by functional blocks.
Figure 13:
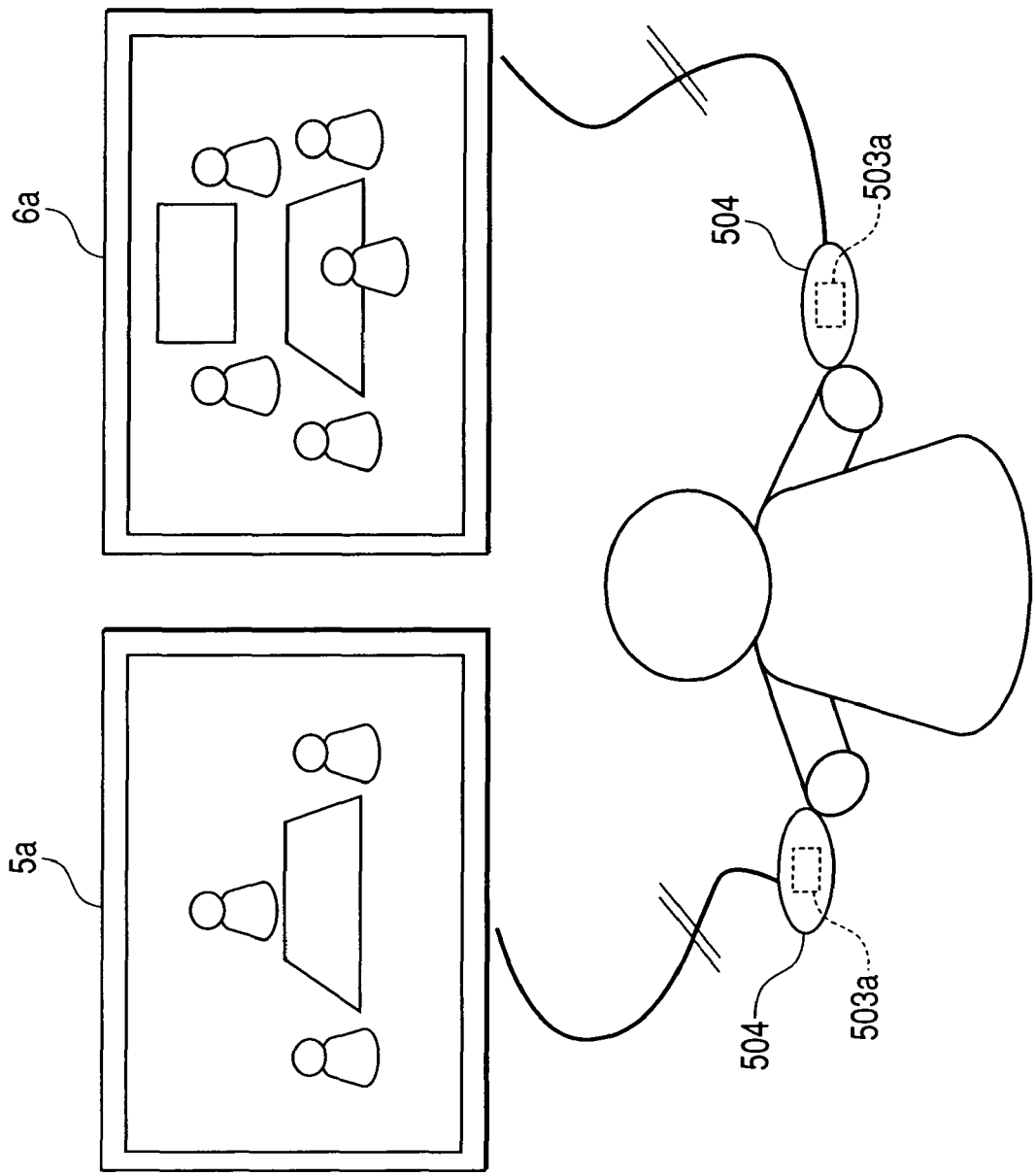
FIG. 13 is a diagram describing an example of an attention calling driving part of the second embodiment.

In FIG. 12, the interference avoidance type display part 502 is provided with an attention calling driving part 503 for adopting a presentation format for avoiding the fear of interfering with the primary job and applying a further recognition load to a user in the display part 501. The attention calling driving part 503 is portion for calling user's attention by working on a user by physical action or chemical action such as mechanical vibration or delivery of a blow and, for example, as shown in FIG. 13, a vibration driving part 503*a* is adopted as the attention calling driving part 503 and this vibration driving part is attached to a mouse 504 or a pen (not shown) for pointing, etc. and an attention calling action can be detected by vibration transmission from the mouse 504 or the pen, etc. even in a scene in which a user does not look directly at display devices 5*a*, 6*a*, for example, looks at a document of paper. In an example of FIG. 13, the attention calling driving parts 503 (vibration driving parts 503*a*) are disposed in both the mice 504 etc. so as to be able to cope with attention calling to deskwork in a peripheral job as well as attention calling to the peripheral job in the desk work. In the case of vibration, it can instantaneously be detected that the vibration is generated from where, and interference with the primary job is less. In the example of FIG. 13, the mouse 504 or the pen, etc. are disposed every each job, but it may be constructed so that both the jobs can be switched and operated by a single mouse 504 etc. In this case, it is preferable to vary vibration places according to attention calling target jobs.

Incidentally, in FIG. 13 and the later Figs., numeral 5*a* is a display device of a deskwork display part 5 and numeral 6*a* is a display device of a peripheral job display part 6.

Figure 14:
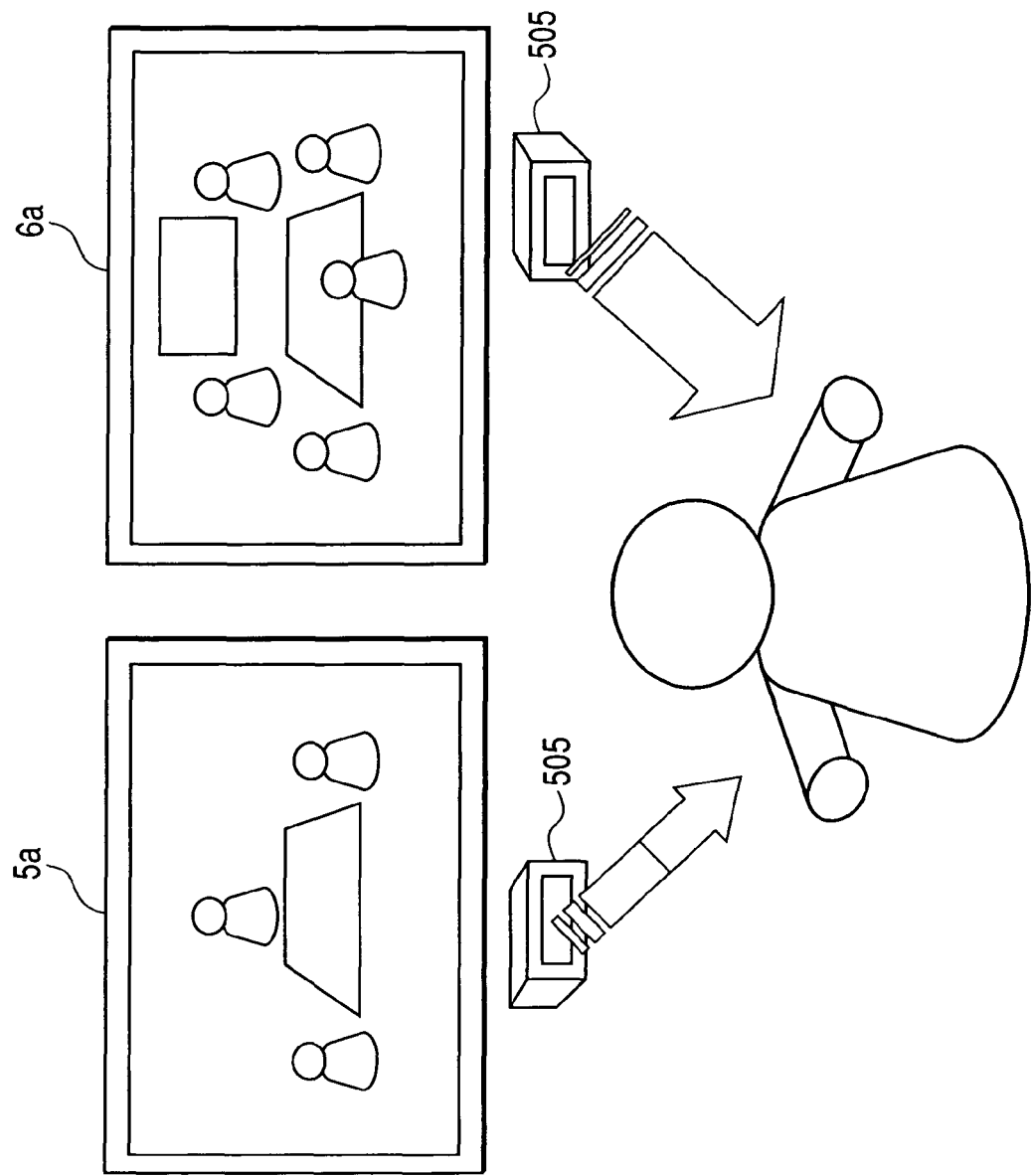
FIG. 14 is a diagram describing another example of an attention calling driving part of the second embodiment.

Or, the attention calling driving part 503 may be based on a temperature change presentation form as shown in FIG. 14. In an example of FIG. 14, a warm-air delivery device 505 is disposed every job. The warm-air delivery device 505 has, for example, a form of telling a high point of a conference, that is, a notable spot as warm air, and attention is called by delivering air from the warm-air delivery device 505 of the corresponding job information side at the time of calling attention. By delivering warm air from the attention calling job side, the warm air can be detected to call user's attention naturally without interfering with the primary job. Of course, it may be a simple blow or cold air rather than the warm air. Also, it may be constructed so that instead of the warm-air delivery device 505, a heat transfer device is disposed and attention is called by a temperature difference.

Also, since the sense of smell is not used basically in many of the primary jobs, it may be constructed so that smell (smell component) is set for attention calling and a smell substance is floated and attention is called to the corresponding job information side.

Figure 15:
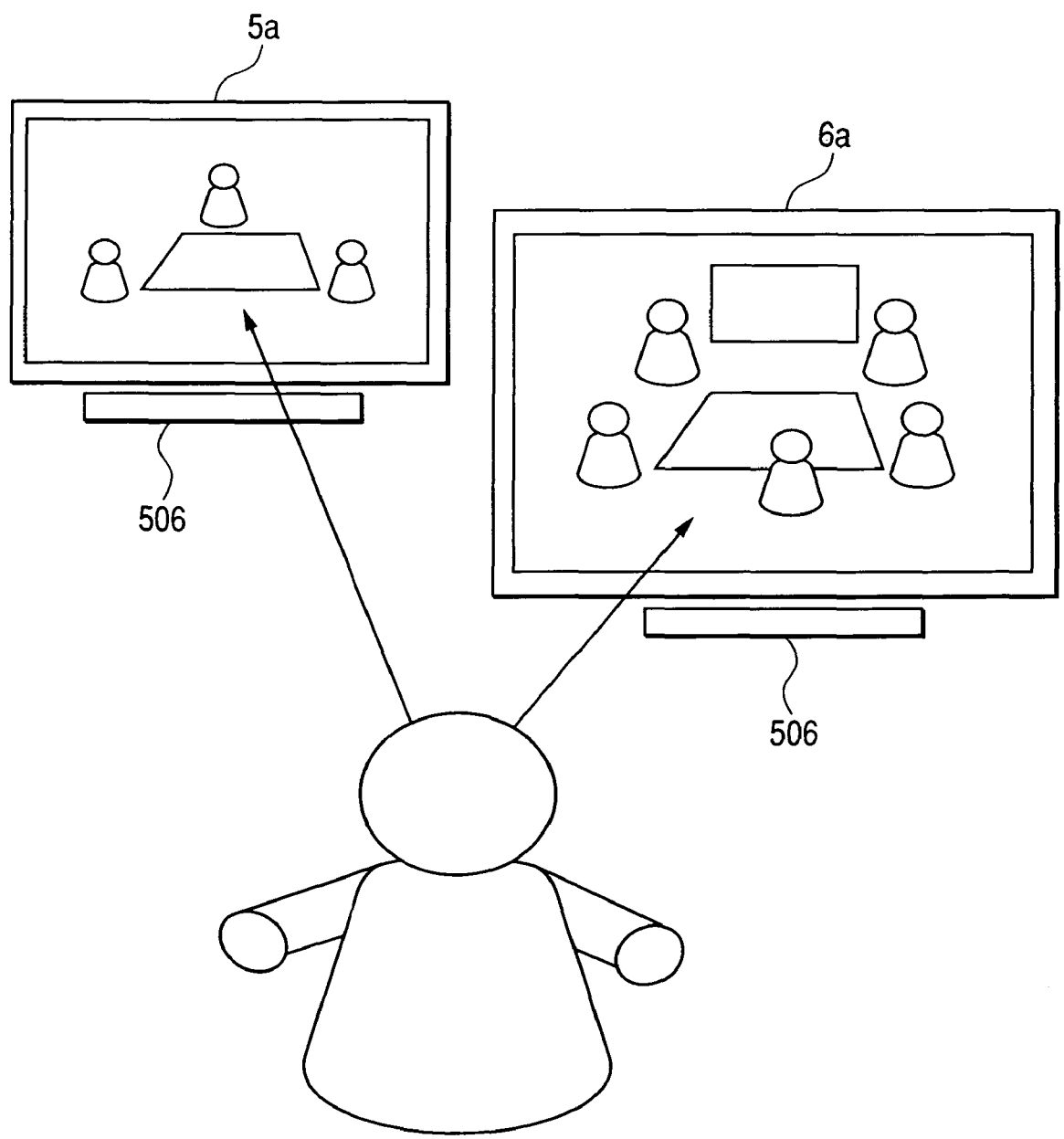
FIG. 15 is a diagram describing an example of a technique for calling attention by altering an audio-visual form in the second embodiment.
Figure 16:
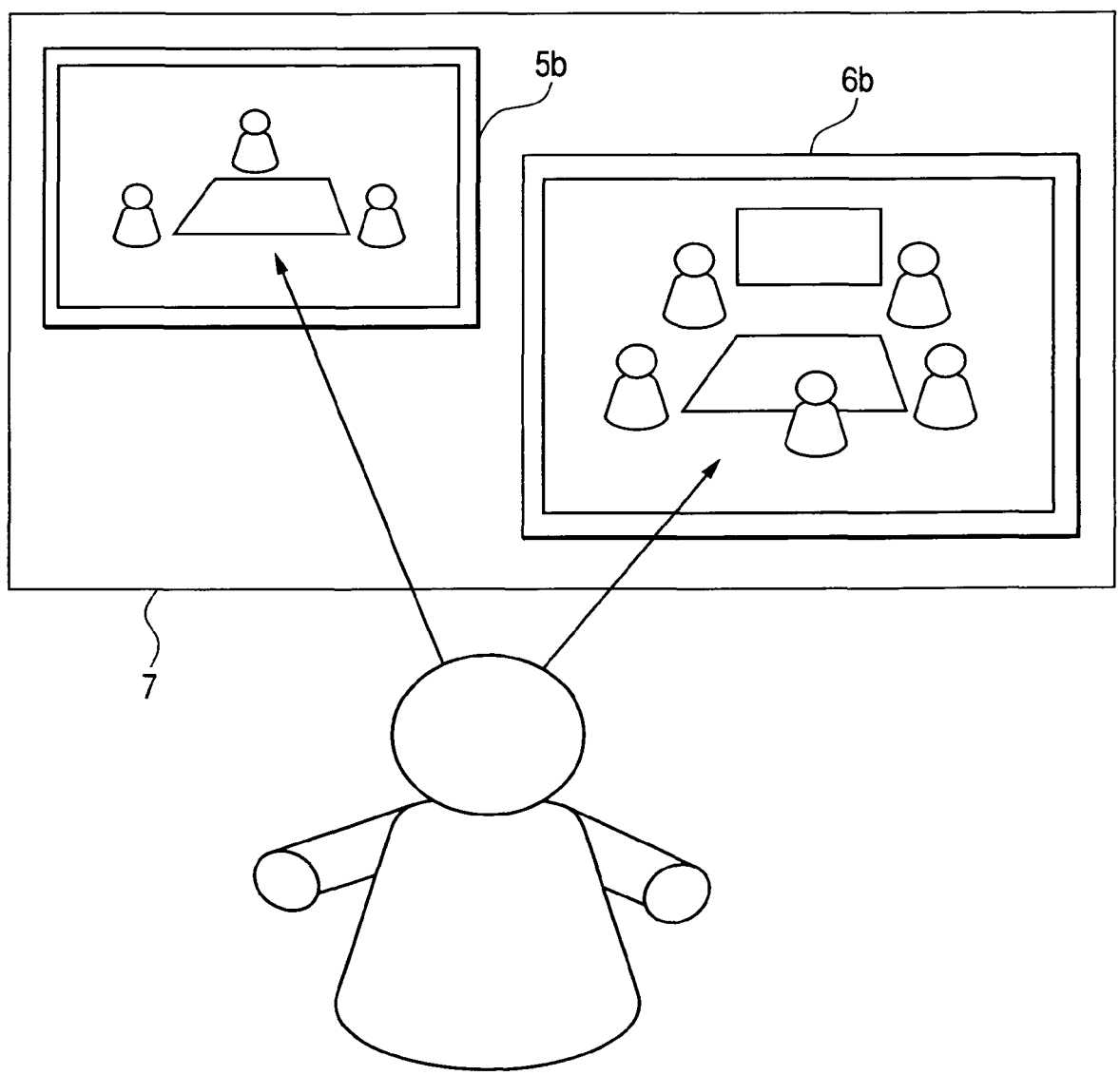
FIG. 16 is a diagram describing an example of another technique for calling attention by altering an audio-visual form in the second embodiment.

Further, user's attention may be called naturally by altering a display form (audio-visual form) rather than using the attention calling driving part 503. In this technique, user's attention is called naturally by the display form (audio-visual form), and interference with the primary job can be avoided more. For example, as shown in FIG. 15, in the case of a display form using plural display devices 5*a*, 6*a*, attention may be called so that display position alteration parts 506 are disposed and a distance between a user and the display device 5*a* or 6*a* requiring the attention calling is altered at a short distance or the other distance is altered at a long distance. In the case of FIG. 15, a position of the display device is physically moved, but as shown in FIG. 16, plural windows 5*b*, 6*b* respectively corresponding to jobs are displayed on a large screen 7 and a size of each of the windows 5*b*, 6*b* is changed and the windows may be displayed as if a display device moved.

Figure 17:
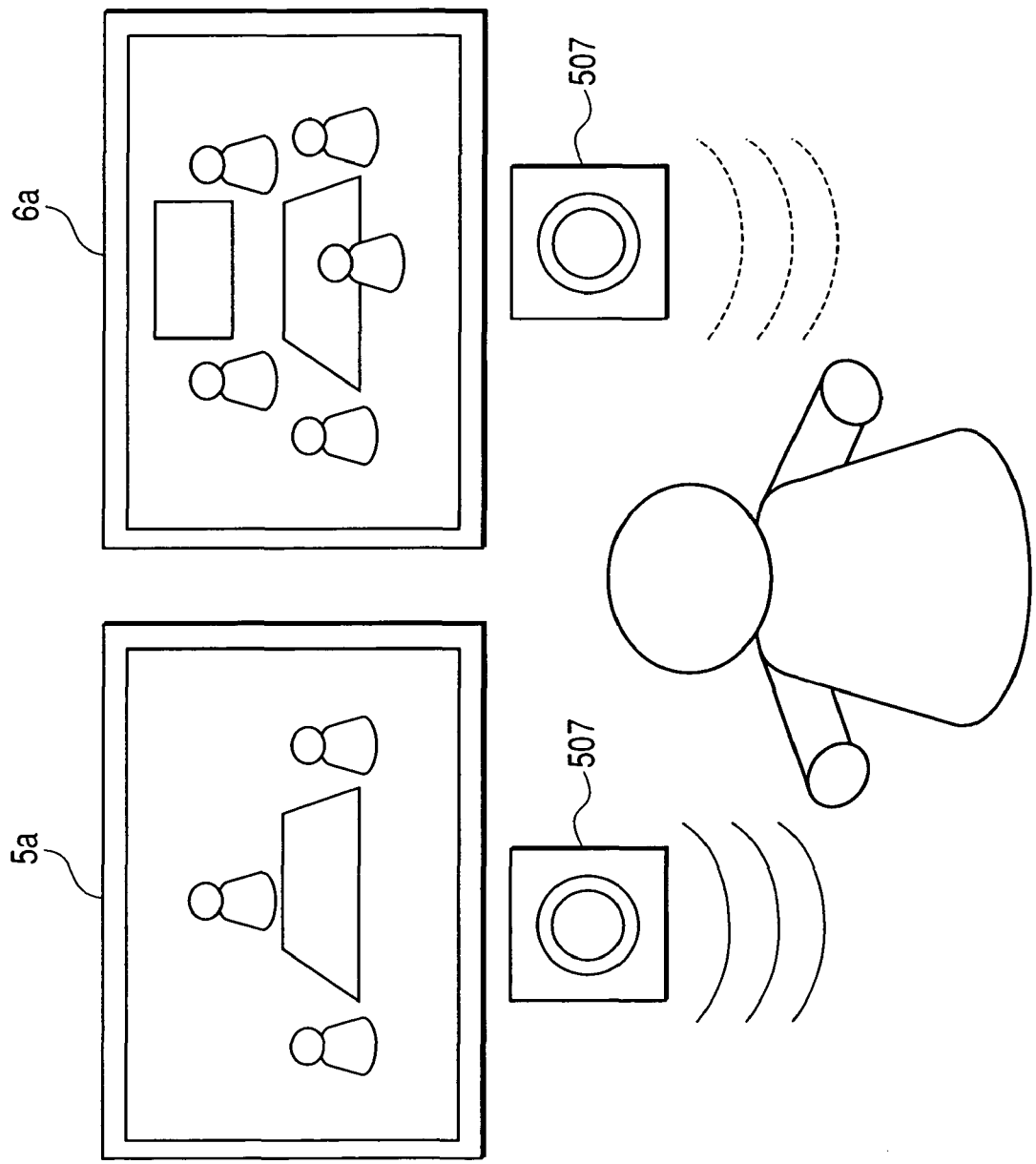
FIG. 17 is a diagram further describing an example of another technique for calling attention by altering an audio-visual form in the second embodiment.

Or, as shown in FIG. 17, it may be constructed so that sound volume alteration parts 507 are disposed and a form in which sound volume of information requiring the attention calling is altered large or the other sound volume is altered small is used, or instead of the sound volume alteration parts 507, sound quality alteration parts are disposed and sound quality of information which does not require the attention calling is altered to the sound quality without deterioration or a harsh sound by, for example, altering a frequency band.

Also, for example, as shown in FIG. 18, it may be constructed so that luminance alteration parts 508 are disposed and luminance of information which does not require the attention calling is decreased and is altered to the luminance without an eyesore and is presented. Also, it may be constructed so that instead of the luminance alteration parts 508, image quality alteration parts are disposed and image quality of information which does not require the attention calling is altered to the image quality without deterioration or an eyesore by, for example, altering the number of pixels or masking. Also, a form in which information presentation delay parts are disposed and information presentation of information which does not require the attention calling is stopped and single tasking is temporarily supported may be used. The delayed information may be presented as it is at the time of resumption later and in some cases, it may be constructed so that rather than delay, information during that span is discarded and information is presented from an event of resumption.

The preferred embodiments of the invention have been described above in detail, but the invention is not limited to the embodiments described above, and can made various modifications and changes. For example, in each of the embodiments described above, a communication status has been described using a conference, but can also be applied to viewing etc. of a video seminar. In this case, audio and video of the video seminar can be analyzed to determine a peripheral job status, so that the need for a detection unit (a measurement unit) can be eliminated. Also, as described above, display of switching is not limited to visual display and may be carried out by, for example, pronunciation, scent or smell. Also, switching of jobs may be done directly by a decision on switching. For example, it may be constructed so that a window of a switching destination is activated when respective jobs perform in each of the windows of multitasking and multi-window environment. Also, in the example described above, it is constructed so that the contents of presentation are displayed on the peripheral job display part 6, but a user may stay on a site of the presentation. Also, there may be three or more jobs of a switching target. Also, in a state in which attention is called so as to do switching and a desired job is performed, attention may be called so as to switch to the original job or another job. For example, in the example described above, attention has been called so as to switch from a deskwork job to a peripheral job, but it may be constructed so that attention is called so as to switch from the peripheral job to the deskwork job.

Also, in the configuration example of FIG. 7, for example, it is constructed so as to control the deskwork display part 5 or the peripheral job display part 6 (electronic teleconference system) by the computing machine 208, and a body of the display system 100 can be mounted in a server device connected to the computing machine 208 through a communication network, but a main part of the display system 100 may be mounted in the computing machine 208.

What is claimed is:

1. An attention calling apparatus comprising:
 a first measurement unit that measures first information indicating human concentration of a first person on a first job which the first person performs as a primary job, wherein the first person performs a second job as a peripheral job while performing the first job, wherein the first job is one of deskwork and a conference and the second job is the other one of said deskwork and said conference;
 a receiving unit that receives, from a second measurement unit, second information indicating human concentration of a second person on the second job which the second person also performs, wherein the second information is measured by the second measurement unit while the first measurement unit measures the first information; and
 an attention calling processing execution unit that executes processing for calling the first person's attention to perform the second job as the primary job based on the first information and the second information.

2. The attention calling apparatus according to claim 1, wherein the attention calling processing execution unit also executes processing for calling the first person's attention to perform the first job.

3. The attention calling apparatus according to claim 1, wherein the second measurement unit selects the second person from among a plurality of persons who perform the second job.

4. The attention calling apparatus according to claim 1, wherein a plurality of persons including the second person perform the second job, and the second measurement unit measures a plurality of the second information with respect to the plurality of the persons.

5. The attention calling apparatus according to claim 1, wherein the first information and the second information indicate at least one of human biological information, human audio information, and human operation processing information.

6. The attention calling apparatus according to claim 5, wherein the human biological information is selected from the group including an electroencephalogram, utterance information, facial skin temperature and information about an eyeball including a blink, a pupil diameter, a gaze target and gaze time.

7. The attention calling apparatus according to claim 5, wherein the human biological information can be measured without attaching a measuring device to a human of a target.

8. The attention calling apparatus according to claim 5, wherein the human audio information is detected by an audio detector.

9. The attention calling apparatus according to claim 5, wherein the human operation processing information is selected from the group including video information, key input information and mouse operation input information.

10. The attention calling apparatus according to claim 1, wherein the first job is said deskwork.

11. The attention calling apparatus according to claim 1, wherein the second job is said conference.

12. The attention calling apparatus according to claim 11, wherein the conference requires (i) participating in the conference using a teleconference system or (ii) attending the conference held at a conference place.

13. The attention calling apparatus according to claim 1, wherein the second job requires audio-visual operation by the second person.

14. The attention calling apparatus according to claim 13, wherein the job requiring the audio-visual operation is viewing of audio-visual contents by the second person.

15. The attention calling apparatus according to claim 1, wherein the attention calling processing execution unit selects the processing for calling the first person's attention from at least one of displaying on a display device, pronouncing by a pronunciation device, and generating smell by a smell generation device.

16. The attention calling apparatus according to claim 1, wherein the first job is executed in a first window displayed in a multi-window system and the second job is executed in a second window of the multi-window system, and the second window of the second job is activated by (i) the processing for calling the first person's attention or (ii) an action by the first person responding to the processing for calling the first person's attention.

17. The attention calling apparatus according to claim 1, wherein the processing for calling the first person's attention by the attention calling processing execution unit is processing for suppressing interference with at least the first job.

18. The attention calling apparatus according to claim 1, wherein the processing for calling the first person's attention by the attention calling processing execution unit is selected from at least one of vibrating by a vibration generation device, changing temperature by a heat transfer device, changing air volume by a blower, and changing a display position by a display position alteration device.

19. The attention calling apparatus according to claim 1, wherein the processing for calling the first person's attention by the attention calling processing execution unit is processing for suppressing the human concentration on the first job by the first person for calling the first person's attention to the second job.

20. The attention calling apparatus according to claim 19, wherein the attention calling processing execution unit executes the processing for suppressing the human concentration on the first job by the first person by altering sound volume, altering sound quality, altering luminance, or altering image quality.

21. The attention calling apparatus according to claim 1, wherein the processing for calling the first person's attention by the attention calling processing execution unit is processing for delaying provision of information related to the first job to the first person so that the first person stops performing the first job.

22. An attention calling method comprising:
  measuring, using a first measuring unit, first information indicating human concentration of a first person on a first job which the first person performs as a primary job, wherein the first person performs a second job as a peripheral job while performing the first job, wherein the first job is one of deskwork and a conference and the second job is the other one of said deskwork and said conference;
  receiving, from a second measuring unit, second information indicating human concentration of a second person on the second job which the second person also performs, wherein the second information is measured by the second measurement unit while the first information is measured by the first measurement unit; and
  executing processing for calling the first person's attention to perform the second job as the primary job based on the first information and the second information.

23. A non-transitory computer readable storage medium storing a computer program for attention calling, the computer program making a computer execute functions comprising:
  measuring, using a first measuring unit, first information indicating human concentration of a first person on a first job which the first person performs as a primary job, wherein the first person performs a second job as a peripheral job while performing the first job, wherein the first job is one of deskwork and a conference and the second job is the other one of said deskwork and said conference;
  receiving, from a second measuring unit, second information indicating human concentration of a second person on the second job which the second person performs, wherein the second information is measured by the second measurement unit while the first information is measured by the first measurement unit; and
  executing processing for calling the first person's attention to perform the second job as the primary job based on the first information and the second information.

24. An information processing system comprising:
an information processing unit for carrying out information processing for a first job performed by a first person;
a first measurement unit that measures first information indicating human concentration of the first person on the first job which the first person performs as a primary job, wherein the first person performs a second job as a peripheral job while performing the first job, wherein the first job is one of deskwork and a conference and the second job is the other one of said deskwork and said conference;
a second measuring unit that measures second information indicating human concentration of a second person on the second job which the second person performs, wherein the second information is measured by the second measurement unit while the first measurement unit measures the first information; and
an attention calling processing execution unit that executes processing for calling the first person's attention to perform the second job as the primary job based on the first information and the second information.

25. The attention calling apparatus according to claim 1, wherein the first job is the deskwork and the second job is the conference.

26. The attention calling method according to claim 22, wherein the first job is the deskwork and the second job is the conference.

27. The computer program for attention calling according to claim 23, wherein the first job is the deskwork and the second job is the conference.

28. The information processing system according to claim 24, wherein the first job is the deskwork and the second job is the conference.

29. The attention calling apparatus according to claim 21, wherein the attention calling processing execution unit executes the delaying the provision of information related to the first job by stopping presentation of information related to the first job to the first person and the delayed information is presented to the first person when the first job is resumed.

* * * * *